United States Patent

Kanayama et al.

[11] Patent Number: 5,371,236
[45] Date of Patent: Dec. 6, 1994

[54] NON-CRYSTALLINE ETHER-IMIDE TYPE HIGH PURITY BISMALEIMIDE COMPOSITION AND PROCESS FOR PRODUCING THE SAME

[75] Inventors: Kaoru Kanayama; Tadao Takeyama; Takeshi Nakato; Yoshinobu Ohnuma; Hiromi Chiba, all of Ibaraki, Japan

[73] Assignee: Mitsubishi Petrochemical Co., Ltd., Tokyo, Japan

[21] Appl. No.: 77,763

[22] Filed: Jun. 18, 1993

[30] Foreign Application Priority Data

Jun. 18, 1992 [JP] Japan .................................. 4-159551
Oct. 19, 1992 [JP] Japan .................................. 4-280174

[51] Int. Cl.$^5$ ............................................ C07D 403/10
[52] U.S. Cl. ..................................... 548/521; 548/522
[58] Field of Search ................................ 548/521, 522

[56] References Cited

FOREIGN PATENT DOCUMENTS 0109262 11/1983 Japan .

Primary Examiner—David R. Springer
Attorney, Agent, or Firm—Oblon, Spivak, McClelland, Maier & Neustadt

[57] ABSTRACT

A non-crystalline ether-imide type high purity bismaleimide composition represented by formula (I):

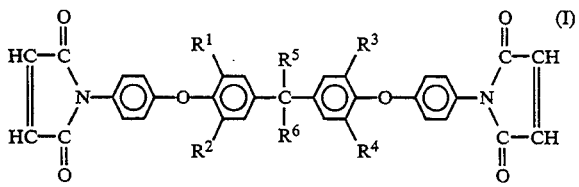

wherein $R^1$, $R^2$, $R^3$, and $R^4$ each represent a hydrogen atom, a halogen atom, or an alkyl group having from 1 to 4 carbon atoms; $R^5$ represents a hydrogen atom or a methyl group; and $R^6$ represents a hydrogen atom, a methyl group or a phenyl group. The non-crystalline bismaleimide (I) has a purity of 95 wt % or higher, a melting point of not higher than 130° C., and exhibits excellent solubility in a solvent. It is prepared by a process comprising uniformly melting a crystalline bismaleimide (I) followed by rapid cooling to solidify or a process comprising subjecting a maleamic acid, which is obtained by addition reaction between a corresponding aromatic ether diamine and maleic anhydride in an aromatic hydrocarbon/aprotic polar solvent mixed solvent, to dehydrating cyclization in the presence of an acid catalyst while azeotropically removing by-produced water with the aromatic hydrocarbon solvent, removing the remaining aromatic hydrocarbon solvent by distillation, withdrawing the produced maleimide in a molten state, and rapidly cooling to solidify.

7 Claims, 5 Drawing Sheets

NON-CRYSTALLINE ETHER-IMIDE TYPE HIGH PURITY BISMALEIMIDE COMPOSITION AND PROCESS FOR PRODUCING THE SAME

FIELD OF THE INVENTION

This invention relates to a non-crystalline ether-imide type bismaleimide composition having high purity, high heat resistance, and excellent workability due to satisfactory solubility in a solvent and useful as a sealing material, a laminating material, an electrical insulating material, a molding material, a conductive paste, an adhesive, etc.

BACKGROUND OF THE INVENTION

Known processes for producing an ether-imide type bismaleimide, e.g., 2,2-bis[4-(4-maleimidophenoxy)phenyl]propane, typically include a dehydrating cyclization reaction of a corresponding maleamic acid using a dehydrating agent (e.g., acetic anhydride) in a ketone solvent (e.g., acetone) or a polar solvent (e.g., N,N-dimethylformamide) in the presence of a base (e.g., triethylamine) and a metallic compound (see U.S. Pat. No. 4,460,783). However, this process does not achieve sufficient progress of the cyclization reaction, only to provide a bismaleimide containing a considerable amount of uncyclized maleamic acid. Therefore, while the resulting bismaleimide is soluble in organic solvents, such as acetone, toluene, methyl ethyl ketone, etc., it liberates water on curing due to the uncyclized maleamic acid and other impurities such as an addition product between the bismaleimide and acetic anhydride, and resulting cured product suffers from voids or blisters or has a reduced glass transition temperature and so deteriorated heat resistance.

R. H. Dahmas has obtained a high purity and substantially acetone-insoluble ether-imide type bismaleimide by dissolving the above-described imidation product in acetone followed by selective re-precipitation and proposed an acetone solution of a mixture of the resulting high purity acetone-insoluble ether-imide type bismaleimide, a corresponding precursor maleamic acid, and a polyamine of an amount required for neutralizing the maleamic acid as a composition suitable for a bismaleimide resin matrix composite (see U.S. Pat. Nos. 4,808,646, 4,816,512 and 4,924,005).

On the other hand, it is also known to prepare a bismaleimide by a process comprising addition reaction between an aromatic diamine corresponding to an ether-imide type bismaleimide and maleic anhydride in a mixed solvent of an aromatic hydrocarbon and an aprotic polar solvent at a low temperature to obtain a bismaleamic acid in accordance with a known process for producing a highly crystalline aromatic bismaleimide (e.g., N,N-(4,4'-diphenylmethane)bismaleimide) (see JP-A-60-260623 and JP-A-63-301226, the term "JP-A" as used herein means an "unexamined published Japanese patent application") and then subjecting the resulting bismaleamic acid to dehydrating cyclization using an acid catalyst (see JP-A-1-211563). According to this process, the cyclization reaction does not proceed sufficiently, and a considerable amount of the bismaleamic acid remains uncyclized in the resulting bismaleimide. If an ether-imide type bismaleimide is crystallized in an aromatic hydrocarbon solvent, the solvent will be included in the precipitated crystals. Hence, for obtaining a high purity product, recrystallization must be conducted in a low-boiling halogenated hydrocarbon solvent (see JP-A-1-238568).

A process comprising dissolving a bismaleimide obtained by drying in tetrahydrofuran or acetone and re-precipitating in water is also known (see JP-A-3-145462). High purity 2,2-bis[4-(4-maleimidophenoxy)phenyl]propane obtained by recrystallization as in the above process is highly crystalline similarly to a highly crystalline aromatic bismaleimide, such as N,N-(4,4'-diphenylmethane)bismaleimide, and therefore has low solubility in a solvent and also a high melting point.

Having excellent heat resistance, a polymaleimide resin is used as a heat resistant modifier for thermosetting resins, such as epoxy resins and vinyl compounds. Where a highly crystalline and high-melting maleimide is used in combination with these reactive liquid resins, it has poor workability in that it is apt to crystallize in the resin solution, requires a high temperature for forming the resin solution, and causes gelation or volatilization of a solvent.

SUMMARY OF THE INVENTION

Accordingly, an object of the present invention is to provide an ether-imide type bismaleimide which has a high purity and comprises a non-crystalline bismaleimide and therefore exhibits a low melting point and excellent solubility in a solvent.

Another object of the present invention is to provide a process for producing the above-mentioned bismaleimide.

The present invention relates to a non-crystalline, ether-imide type high purity bismaleimide composition represented by formula (I):

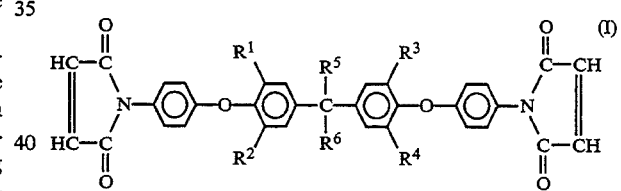

wherein $R^1$, $R^2$, $R^3$, and $R^4$ each represent a hydrogen atom, a halogen atom, or an alkyl group having from 1 to 4 carbon atoms; $R^5$ represents a hydrogen atom or a methyl group; and $R^6$ represents a hydrogen atom, a methyl group or a phenyl group.

The present invention also relates to a process for producing the above-described bismaleimide composition comprising uniformly melting a crystalline bismaleimide represented by formula (I) and rapidly cooling the molten bismaleimide to solidify.

The present invention further relates to a process for producing the above-described bismaleimide composition comprising addition reacting an aromatic ether diamine represented by formula (II):

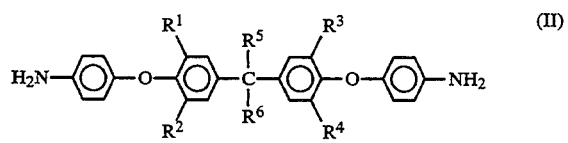

wherein $R^1$, $R^2$, $R^3$, $R^4$, $R^5$, and $R^6$ are as defined in formula (I), and maleic anhydride in a mixed solvent of an aromatic hydrocarbon solvent and an aprotic polar solvent to obtain a maleamic acid, subjecting the resulting maleamic acid to dehydrating cyclization in the presence of an acid catalyst while azeotropically removing by-produced water with the aromatic hydrocarbon solvent, removing the remaining aromatic hydrocarbon solvent by distillation at a temperature of from 40° to 200° C., withdrawing the produced maleimide in a molten state, and rapidly cooling the maleimide to solidify.

DETAILED DESCRIPTION OF THE INVENTION

Figure 1:
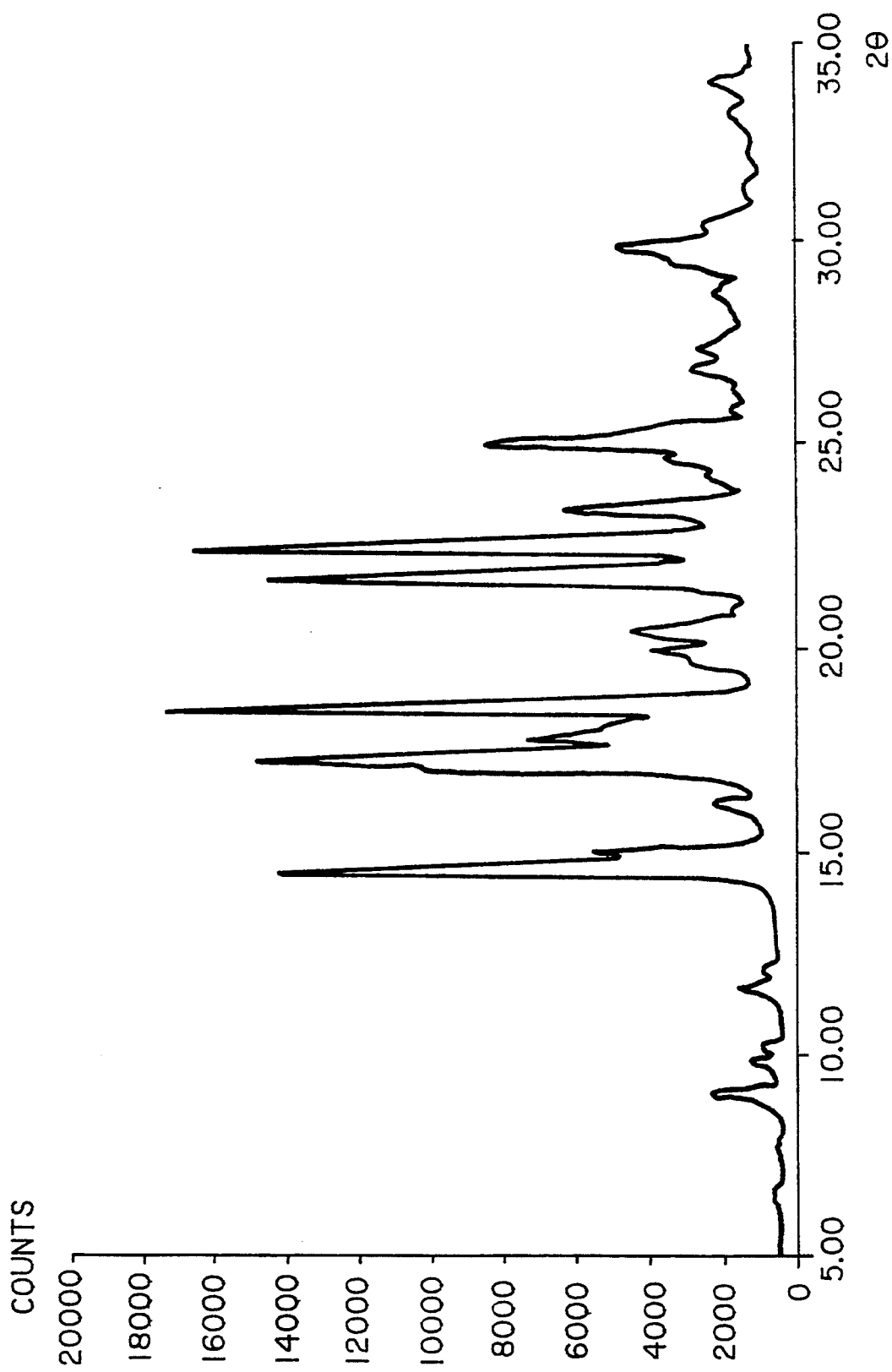
FIG. 1 is an X-ray diffraction spectrum of highly crystalline 2,2-bis[4-(4-maleimidophenoxy)phenyl]propane used in Example 1.
Figure 2:
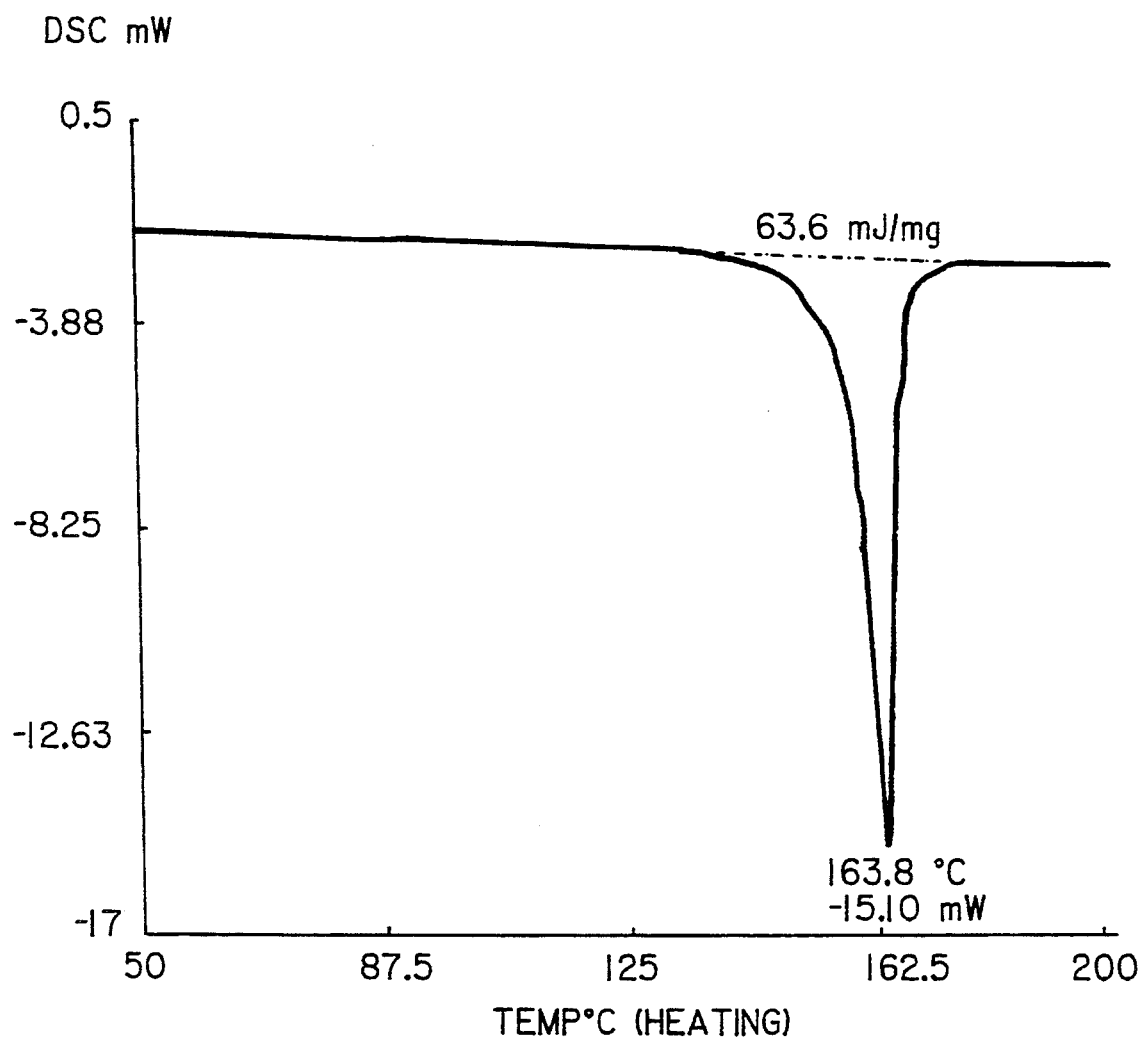
FIG. 2 is a thermogram of the highly crystalline 2,2-bis[4-(4-maleimidophenoxy)phenyl]propane used in Example 1 as measured with a differential scanning calorimeter (DSC).
Figure 3:
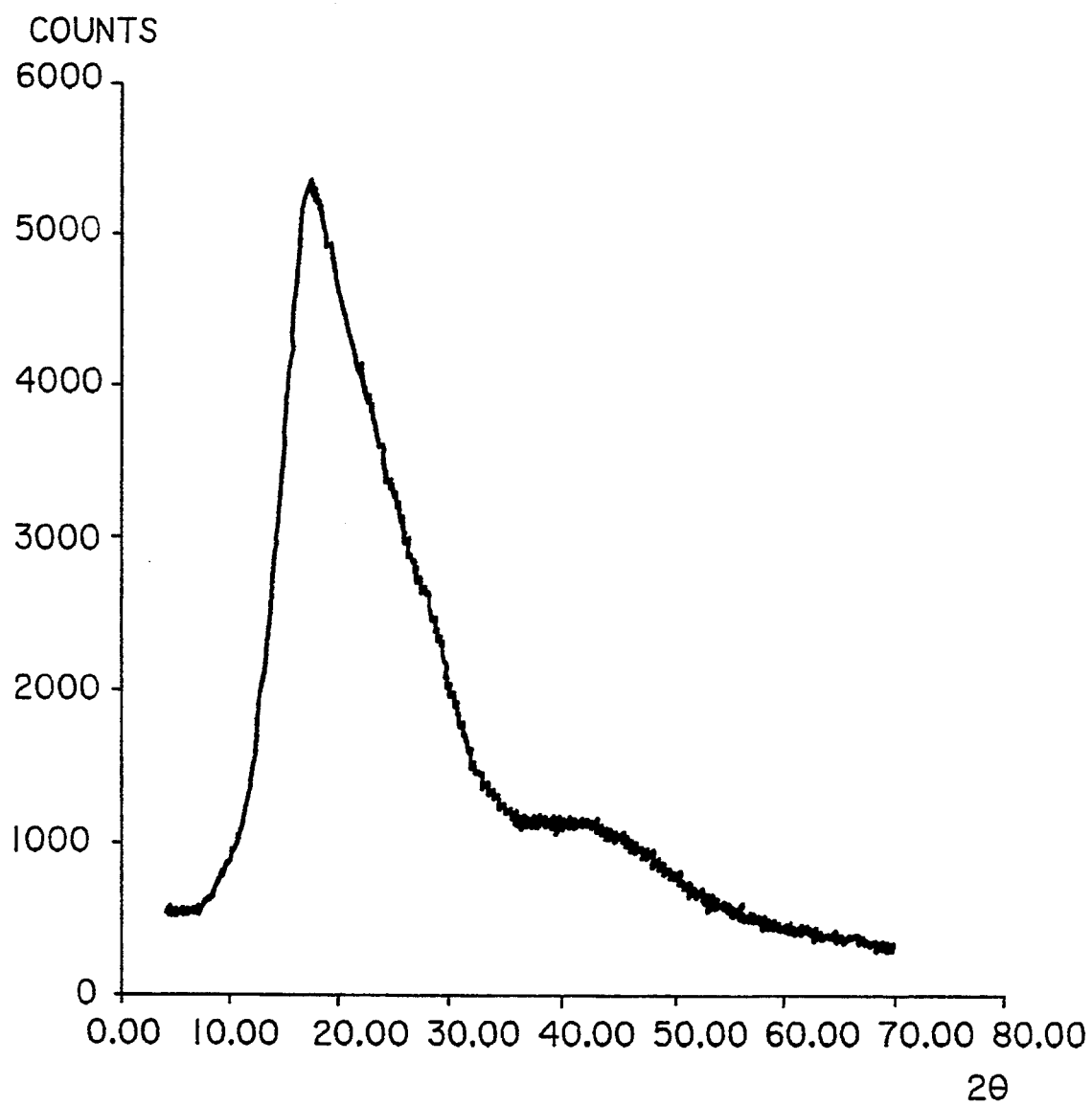
FIG. 3 is an X-ray diffraction spectrum of the non-crystalline bismaleimide resin obtained in Example 1.
Figure 4:
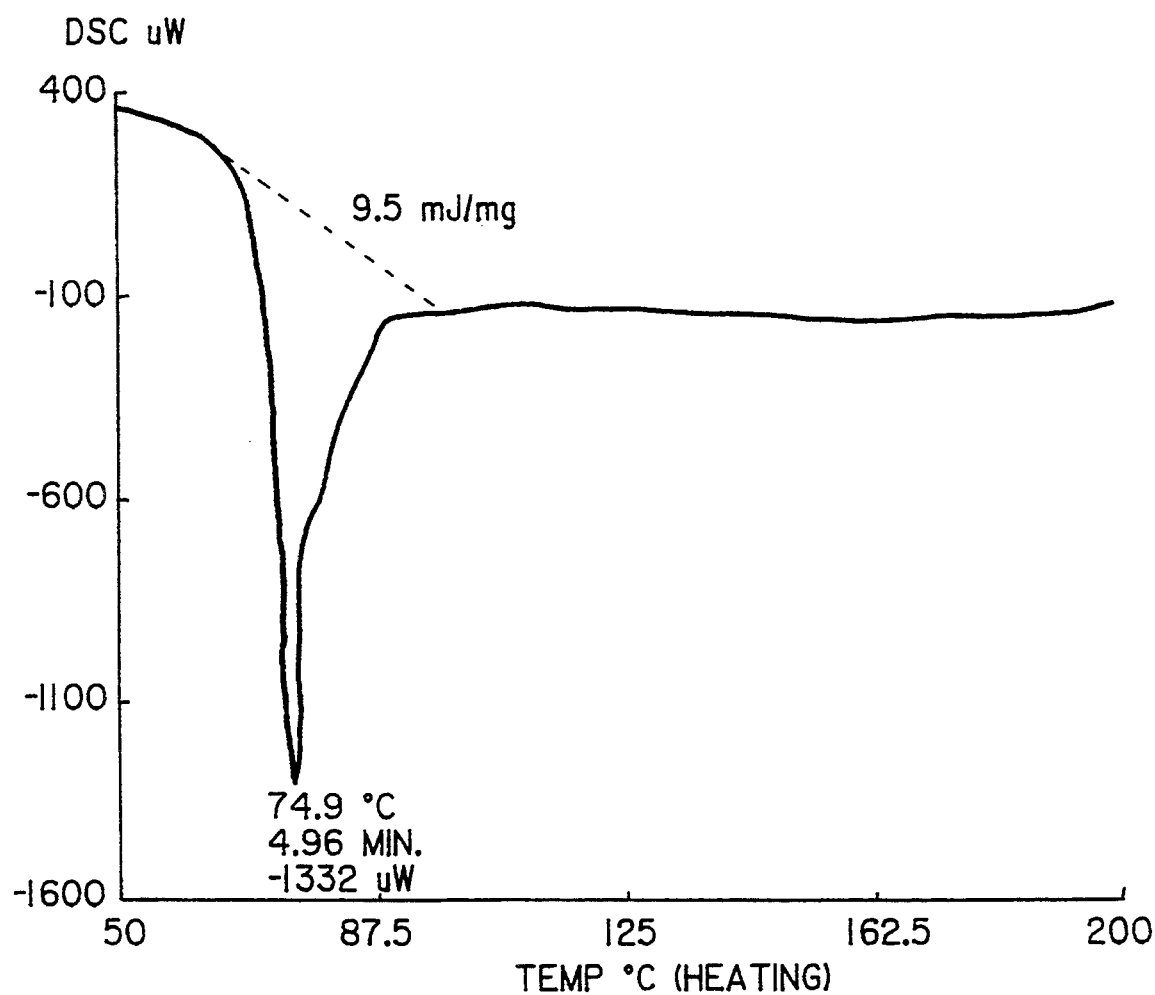
FIG. 4 is a DSC thermogram of the non-crystalline bismaleimide resin obtained in Example 1.
Figure 5:
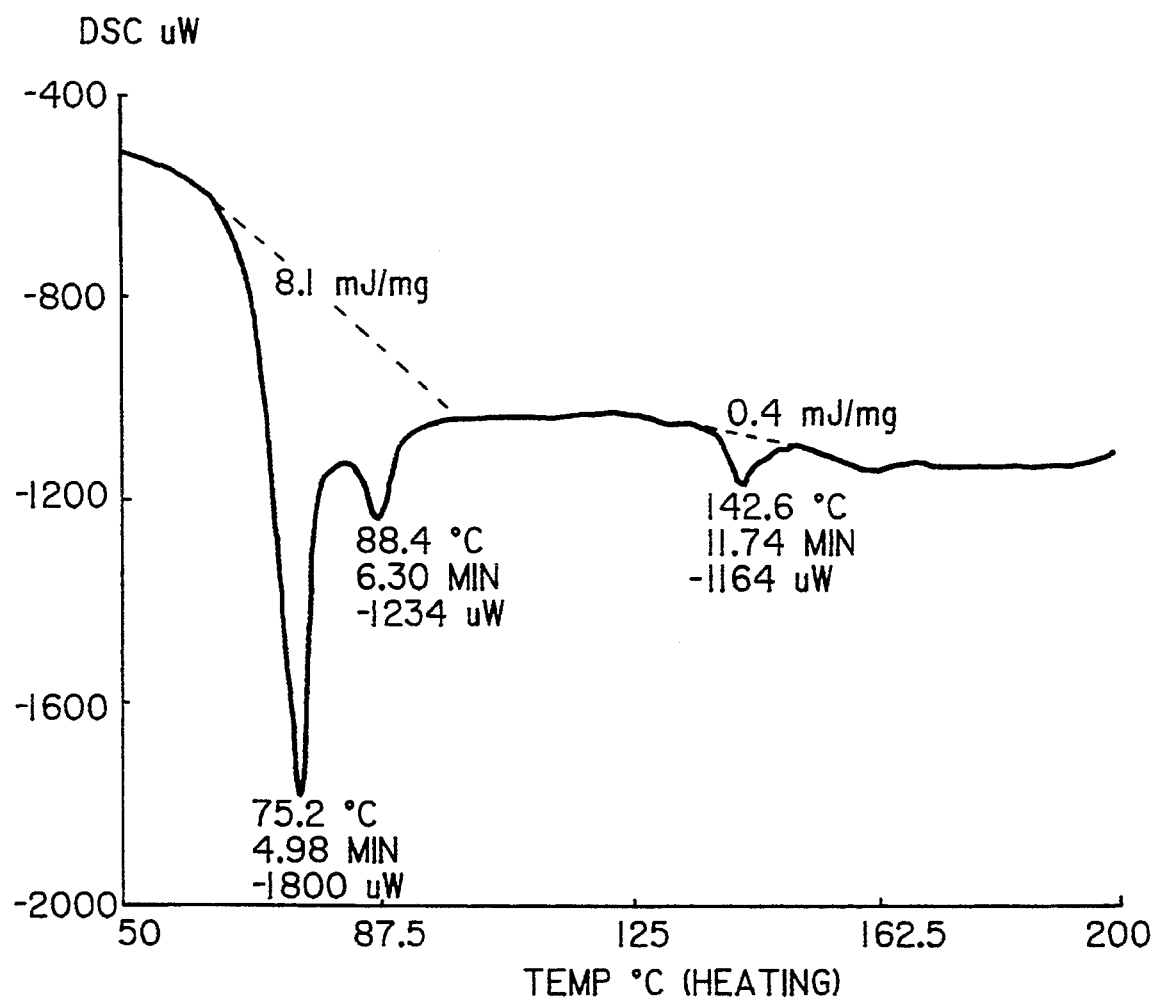
FIG. 5 is a DSC thermogram of the non-crystalline bismaleimide resin obtained in Example 2.

Specific examples of the bismaleimide represented by formula (I) include 1,1-bis[4-(4-maleimidophenoxy)phenyl]methane, 2,2-bis[4-(4-maleimidophenoxy)phenyl]propane, 2,2-bis[3-methyl-4-(4-maleimidophenoxy)phenyl]propane, 2,2-bis[3-butyl-4-(4-maleimidophenoxy)phenyl]propane, 2,2-bis[3,5-dimethyl-4-(4-maleimidophenoxy)phenyl]propane, 1-phenyl-1,1-bis[4-(4-maleimidophenoxy)phenyl]ethane, and 1-phenyl-1,1-bis[3,5-dimethyl-4-(4-maleimidophenoxy)phenyl]ethane.

As described above, while a high purity bismaleimide can be prepared by recrystallization of a bismaleimide obtained by reacting a corresponding aromatic ether diamine and maleic anhydride in a known manner, such a bismaleimide is a crystalline compound which has a melting point usually between 130° and 300° C. and shows a peak of heat of fusion at 120° C. or higher in DSC measurement.

To the contrary, the ether-imide type bismaleimide according to the present invention contains a non-crystalline bismaleimide while having a purity as high as 95% by weight or more. Therefore, it exhibits excellent solubility in a solvent and, in addition, has a melting point of not higher than 130° C. For example, crystalline 1,1-bis[4-(4-maleimidophenoxy)phenyl]methane has a melting point of from 135° to 150° C., while that containing a non-crystalline compound according to the present invention has a melting point of from 60° to 80° C. The ether-imide imide bismaleimide composition of the present invention has a non-crystalline content of at least 50% by weight, and preferably 60% by weight or more. As a result, it shows a peak of heat of fusion at 75°±5° C. and/or 85°±5° C. in DSC measurement, with the ratio of the peak area in temperatures of 120° C. or higher to the total peak area being not more than 50%, and preferably not more than 40%. If the proportion of a non-crystalline bismaleimide is less than 50% by weight, the bismaleimide composition has insufficient stability, showing liability to recrystallization, and insufficient solubility in a solvent.

The above-mentioned non-crystalline ether-imide type bismaleimide can be obtained by, for example, uniformly melt-kneading a crystalline bismaleimide obtained by a known technique, such as recrystallization, followed by rapid cooling to solidify. In greater detail, a crystalline bismaleimide is melt-kneaded in a commonly employed kneading machine, such as a two-roll mill, a Ko-kneader, an extruder, etc., at a temperature of from the melting point of the crystalline bismaleimide up to 250° C. and then rapidly cooled at a cooling rate of not less than 0.1° C./min, and preferably 5° C./min or more, by means of a cooling belt, etc. to solidify. If kneaded at 250° C. or higher temperatures, the bismaleimide tends to undergo crosslinking. If the cooling rate is less than 0.1° C./min, the bismaleimide tends to recrystallize, failing to obtain a non-crystalline bismaleimide composition.

In addition to the above-mentioned melt-kneading process, the non-crystalline bismaleimide composition of the present invention can also be prepared by uniformly dissolving a crystalline bismaleimide in an organic solvent, heating the solution at 80° C. or higher to distill off the organic solvent, and cooling the molten residue to solidify. In more detail, a crystalline bismaleimide is dissolved in an organic solvent by stirring at a temperature of from 20° to 200° C. to form a uniform solution. The organic solvent which can be used includes aromatic hydrocarbons, halogenated hydrocarbons, esters, ketones and aprotic polar solvents. The organic solvent is used in an amount of from 0.4 to 20 parts by weight, preferably 0.6 to 10 parts by weight, per part by weight of the crystalline bismaleimide. The organic solvent solution is then heated to a temperature at which the bismaleimide does not crystallize, i.e., not less than 80° C., preferably from 80° to 200° C., and more preferably from 100° to 160° C., under a pressure of from 0.1 to 760 mmHg to distill off the organic solvent.

The heating of the bismaleimide solution is continued until the temperature exceeds the softening point of the bismaleimide while removing the organic solvent and no substantial organic solvent remains, more specifically until the residual solvent content is reduced to 2% by weight or less. If the heating temperature is lower than 80° C., crystals of the bismaleimide are precipitated during the removal of the organic solvent, failing to produce a stable non-crystalline bismaleimide. If it exceeds 200° C., the bismaleimide tends to polymerize.

After distillation of the organic solvent, the molten bismaleimide is withdrawn from the bottom of the reactor, followed by cooling.

Alternatively, the above-mentioned organic solvent solution of a crystalline bismaleimide is supplied to a film distillation apparatus, etc. either as such or as concentrated to a concentration of about 90% by weight, and the organic solvent is distilled off at a temperature of not lower than the melting point of the bismaleimide. The molten bismaleimide then is withdrawn from the bottom and rapidly cooled. The cooling of the molten bismaleimide is effected in the same manner as in the above-mentioned melt-kneading process.

Suitable organic solvents for dissolving a crystalline bismaleimide include aromatic hydrocarbons, e.g., benzene, toluene, xylene, ethylbenzene, diethylbenzene, butylbenzene, cumene, and mesitylene; halogenated hydrocarbons, e.g., chloroform, dichloromethane, trichloroethylene, tetrachloroethylene, 1,2-dichloroethane, chlorobenzene, dichlorobenzene, chlorotoluene, trichloroethane, and 1,1,2,2-tetrachloroethane; esters, e.g., ethyl formate, n-butyl formate, ethyl acetate, propyl acetate, n-butyl acetate, isobutyl acetate, sec-hexyl acetate, 2-ethylhexyl acetate, ethyl propionate, n-butyl propionate, and ethyl isovalerate; ethers, e.g., diethyl ether, di-n-butyl ether, tetrahydrofuran, 1,4-dioxane, ethylene glycol monomethyl ether, ethylene glycol monoethyl ether, ethylene glycol monobutyl ether, diethylene glycol monoethyl ether, and diethylene glycol mono n-butyl ether; ketones, e.g., acetone, methyl ethyl ketone, methyl isobutyl ketone, and cyclohexanone; and aprotic polar solvents, e.g., N,N-dimethylformamide, N,N-dimethylacetamide, N-methyl-2-pyrrolidone, dimethyl sulfoxide, hexamethylphosphoramide, monoglyme, and diglyme. Preferred of them are aromatic hydrocarbons.

The non-crystalline ether-imide type high purity bismaleimide composition of the present invention can also be prepared directly from a corresponding aromatic ether diamine and maleic anhydride without using a crystalline bismaleimide.

That is, high purity and non-crystalline ether-imide type bismaleimide having excellent solubility can easily be prepared by a process comprising addition reacting an aromatic ether diamine represented by formula (II):

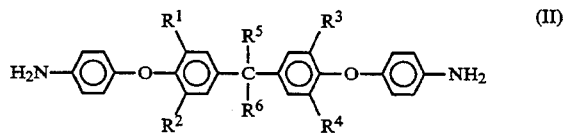

wherein $R^1$, $R^2$, $R^3$, $R^4$, $R^5$, and $R^6$ are as defined in formula (I), and maleic anhydride in a mixed solvent of an aromatic hydrocarbon solvent and an aprotic polar solvent to obtain a maleamic acid, subjecting the resulting maleamic acid to dehydrating cyclization in the presence of an acid catalyst while azeotropically removing by-produced water with the aromatic hydrocarbon solvent, removing the remaining aromatic hydrocarbon solvent by distillation, withdrawing the produced maleimide in a molten state, and rapidly cooling the maleimide to solidify.

Examples of the aromatic ether diamine represented by formula (II) are 1,1-bis[4-(4-aminophenoxy)-phenyl]methane, 2,2-bis[4-(4-aminophenoxy)phenyl]-propane, 2,2-bis[3-methyl-4-(4-aminophenoxy)phenyl]-propane, 2,2-bis[3-butyl-4-(4-aminophenoxy)phenyl]-propane, 2,2-bis[3,5-dimethyl-4-(4-aminophenoxy)-phenyl]propane, 1-phenyl-1,1-bis[3,5-dimethyl-4-(4-aminophenoxy)phenyl]ethane, and 1-phenyl-1,1-bis[4-(4-aminophenoxy)phenyl]ethane.

Maleic anhydride is used in an amount of from 0.9 to 5 mols, and preferably from 1.0 to 1.3 mols, per equivalent of the total amino group in the aromatic ether diamine (II).

Suitable aromatic hydrocarbons to be used in the mixed solvent include those having from 6 to 10 carbon atoms, e.g., benzene, toluene, xylene, ethylbenzene, diethylbenzene, butylbenzene, cumene, and mesitylene, with toluene and xylene being particularly preferred.

Suitable aprotic polar solvents to be combined with the aromatic hydrocarbon include those capable of dissolving the produced maleamic acid, such as amide compounds, e.g., N,N-dimethylformamide, N,N-dimethylacetamide, N-methyl-2-pyrrolidone, 1,3-dimethyl-2-imidazolidinone, and tetramethylurea; sulfur-containing compounds, e.g., dimethyl sulfoxide; and phosphorus-containing compounds, e.g., hexamethylphosphoramide. Of these aprotic polar solvents preferred are those having a boiling point of not lower than 150° C. and hardly forming an azeotrope with water. From this viewpoint, the amide compounds are preferred.

Since part of the aprotic polar solvent used remains in the final product, it is desirably used in the lowest proportion possible in the mixed solvent, usually in a proportion of from 0.1 to 30% by weight, and preferably of from 1 to 20% by weight, based on the total solvent.

The mixed solvent is used in an amount of from 1 to 50 parts by weight, and preferably from 2 to 20 parts by weight, per part by weight of the aromatic diamine.

The addition reaction is usually carried out by dropwise adding a solution of the aromatic diamine in the mixed solvent to a solution of maleic anhydride in an aromatic hydrocarbon solvent at a prescribed temperature. The reaction temperature is from 0° to 200° C., and preferably from 70° to 150° C., and the time of dropwise addition is from 0.5 to 5 hours. After the dropwise addition, the reaction is further continued at the same temperature, preferably from 70° to 150° C., for an additional period of from 0.1 to 5 hours to prepare a slurry of a bismaleamic acid. It is important that the aromatic diamine be completely reacted with maleic anhydride into a bismaleamic acid. Should the reaction temperature be too low or the reaction time be too short, the production ratio of a monomaleamic acid would exceed 5% by weight, which necessitates removal of the monomaleamic acid after dehydrating cyclization in order to obtain a high purity bismaleimide.

After the addition reaction, an acid catalyst is added to the reaction mixture to conduct dehydrating cyclization. Suitable acid catalysts which can be used in the dehydrating cyclization reaction include inorganic acids, e.g., sulfuric acid, sulfuric anhydride, phosphoric acid, polyphosphoric acid, metaphosphoric acid, and condensed phosphoric acid; and organic acids, e.g., p-toluenesulfonic acid, trichloroacetic acid, trifluoroacetic acid, and trifluoromethanesulfonic acid; with the organic acids being preferred.

The acid catalyst is added in an amount of from 0.0001 to 1 mol, and preferably from 0.001 to 0.5 mol, per equivalent of the total amino group in the aromatic polyamine used.

The dehydrating cyclization reaction is carried out at a temperature of from 80° to 200° C., and preferably from 80° to 150° C., under a pressure of from 50 to 760 mmHg while azeotropically removing produced water together with the reaction solvent. The reaction is usually continued for a period of from 1 to 20 hours until the bismaleamic acid substantially disappears. Disappearance of the bismaleamic acid can be observed as a change of the reaction system from a heterogeneous system into a homogeneous system. The solvent recovered as an azeotrope with by-produced water is cooled, separated from water, and returned to the reaction system.

The resulting reaction mixture is distilled at 40° to 200° C., preferably from 80° to 160° C. maintaining a uniform solution to remove the aromatic hydrocarbon solvent. The maleimide produced is withdrawn in a molten state and rapidly cooled to solidify. There is thus obtained a non-crystalline ether-imide type bismaleimide having excellent solubility and high purity.

Before the cyclization reaction mixture is subjected to the above-mentioned working-up procedure, it is preferably washed with water to remove the catalyst, etc. Washing is carried out by adding 0.1 to 20 parts by weight, and preferably 2 to 20 parts by weight, of water per part by weight of the produced maleimide in the reaction mixture, stirring at 70° to 95° C. at 30 to 300 rpm for 3 to 30 minutes, allowing the mixture to stand, followed by liquid-liquid separation. The washing is conducted once or repeated 2 to 5 times, preferably twice or more.

The step of distillation of the reaction mixture to remove the aromatic hydrocarbon solvent using a film distillation apparatus and the step of rapid cooling of the withdrawn molten maleimide can be carried out in the same manner as in the above-mentioned uniformly dissolving process starting with a crystalline bismaleimide.

The thus solidified bismaleimide is usually ground to an appropriate size according to the end use.

The present invention will now be illustrated in greater detail with reference to Examples, but it should be understood that the present invention is not construed as being limited thereto. All the percents and parts are given by weight unless otherwise specified.

Various physical properties were measured in accordance with the following test methods.

1) Purity and Monomaleamic Acid Content

Measured by liquid chromatography and calculated according to an area percentage method.

2) Residual Solvent Content

Measured by gas chromatography (FID) and calculated according to an absolute calibration curve method.

3) Melting Point

Measured according to a capillary method using a melting point tube ("MP-20" manufactured by Yamato Kagaku Co., Ltd.).

4) Crystal Structure

Analyzed with an X-ray diffractometer ("JDX-3500" manufactured by JEOL Co., Ltd.).

5) Peak of Heat of Fusion and Non-Crystallization Rate

Differential thermal analysis was conducted with a differential scanning calorimeter ("DSC-220" manufactured by Seiko Instruments Inc.) under the following conditions to obtain the peak of heat of fusion and the peak area.

Amount of sample: 10 mg
Rate of temperature rise: 10° C./min
Measuring temperature: 10° to 250° C.
Nitrogen flow rate: 10 ml/min The peak area was obtained by dividing an endothermic energy (mJ) of each peak of fusion by the weight (mg) of the sample. Further, the percentage of the heat of fusion at the peak or peaks at temperatures less than 120° C. based on the total heat of fusion was obtained as a non-crystallization rate.

6) Solubility

In an egg-plant flask were put 30 parts of a maleimide resin and 50 parts of an epoxy resin ("E-828" produced by Yuka Shell Epoxy Co., Ltd.) or an acrylic resin ("A-BAP-4" produced by Shin-Nakamura Chemical Co., Ltd.). The mixture was stirred by means of a stirrer, heated in a water bath at 80° C. for 2 hours, and then cooled to room temperature. The solubility of the bismaleimide was judged by observation with the naked eye and rated "good" (the maleimide resin satisfactorily dissolved at a high rate) or "poor" (the maleimide resin did not dissolve).

7) Preservation Stability

The sample used in the above solubility test was put in a 50 ml-volume bottle and allowed to stand at room temperature for 1 month. Formation of a precipitate was observed with the naked eye, and preservation stability was rated as "good" (no crystal was precipitated) or "poor" (crystals were precipitated).

EXAMPLE 1

One kilogram of highly crystalline 2,2-bis[4-(4-maleimidophenoxy)phenyl]propane having a melting point of 158° to 161° C. and a monomaleamic acid content of 1-6% was melt-kneaded in a two-roll mill at a roll temperature of 170° C. for 5 minutes and then cooled at a rate of 50° C./min to obtain a bismaleimide resin having a non-crystallization rate of 100%.

EXAMPLE 2

A non-crystal bismaleimide resin composition was obtained in the same manner as in Example 1, except for changing the roll temperature to 160° C., the melt-kneading time to 2 minutes, and the cooling rate to 20° C./min.

EXAMPLE 3

A non-crystalline bismaleimide resin was obtained in the same manner as in Example 1, except for using 1 kg of highly crystalline 2,2-bis[3-methyl-4-(4-maleimidophenoxy)phenyl]propane having a melting point of 168° to 170° C. and a monomaleamic acid content of 1.3%.

The characteristics of the non-crystalline bismaleimide resins obtained in Examples 1 to 3 and the highly crystalline bismaleimide used in Example 1 (Reference Example 1) are shown in Table 1 below.

TABLE 1

| | Peak of Heat of Fusion | | Melting Point (°C.) | Solubility | | Preservation Stability | |
|---|---|---|---|---|---|---|---|
| | Temp. (°C.) | Area (mJ/mg) | | Ac* | Ex** | Ac | Ex |
| Example 1 | 75 | 9.5 | 65 | good | good | good | good |
| Example 2 | 75, 88 | 8.1 | 75 | good | good | good | good |
| | 143 | 0.4 | | | | | |
| Example 3 | 75 | 10.2 | 62 | good | good | good | good |
| Reference Example 1 | 164 | 63.6 | 158 | poor | poor | poor | poor |

Note:
Ac*: Acrylic resin "A-BAP-4"
Ex**: Epoxy resin "E-828"

EXAMPLE 4

In a 500 ml four-necked flask equipped with a cooler, thermometer and a stirrer were charged 150 g of the same highly crystalline bismaleimide as used in Example 1 and 150 g of toluene, and the mixture was stirred at 115° C. for 1 hour while refluxing the solvent to prepare a uniform solution. The solution was heated in an oil bath kept at 160° C. under atmospheric pressure to distill off toluene at 116° to 140° C. When the amount of distilled toluene became small, the pressure was reduced to 5 mmHg, and distillation was further continued while maintaining at 140° C. until no more toluene was distilled. The molten bismaleimide was withdrawn into an aluminum tray and cooled at room temperature to solidify to obtain 148.2 g of a yellowish brown bismaleimide.

The resulting bismaleimide had a melting point of 67° to 75° C., a residual solvent content of 0.2%, and a solubility of 50% or more in tetrahydrofuran. The bismaleimide showed a broad X-ray diffraction peak and had a non-crystallization rate of 91%.

EXAMPLE 5

A bismaleimide was obtained in the same manner as in Example 4, except for replacing toluene with 400 g of 1,4-dioxane and setting the initial distillation temperature of the solvent at 104° to 140° C. The resulting bismaleimide had a melting point of 69° to 76° C., a residual solvent content of 0.5%, and a non-crystallization rate of 90%.

EXAMPLE 6

A bismaleimide was obtained in the same manner as in Example 4, except for starting with 150 g of highly crystalline 1-phenyl-1,1-bis[3,5-dimethyl-4-(4-maleimidophenoxy)phenyl]ethane having a melting point of 170° to 172° C. and a monomaleamic acid content of 2.0%, replacing toluene with 100 g of n-butyl acetate, and setting the initial distillation temperature of the solvent at 130° to 150° C. and the temperature of distillation under reduced pressure at 150° C. The resulting bismaleimide had a melting point of 93° to 98° C., a residual solvent content of 0.3%, and a non-crystallization rate of 100%.

COMPARATIVE EXAMPLE 1

The same procedure as in Example 4 was repeated, except that the solvent was distilled off under reduced pressure at 65° to 70° C. in an oil bath kept at 90° C. Because the bismaleimide began to crystalize when 80 g of toluene was distilled off, the subsequent operation was not carried out.

REFERENCE EXAMPLE 2

A bismaleimide was obtained in the same manner as in Example 4, except for starting with 150 g of highly crystalline N,N'-(3,3'-diethyl-5,5'-dimethyl-4,4'-diphenylmethane)bismaleimide having a melting point of 161° to 163° C. and changing the initial distillation temperature to 116° to 170° C. and the temperature of distillation under reduced pressure to 170° C.

The resulting bismaleimide had a melting point of 161° to 163° C. and a residual solvent content of 0.1%. The x-ray diffraction pattern showed a sharp peak. The non-crystallization rate was found to be 0%.

EXAMPLE 7

A 500 ml four-necked flask equipped with a cooler, a thermometer, a stirrer, and a water separator were charged 28.9 g of maleic anhydride and 130 g of toluene, and the inner temperature was adjusted to 80° C. A solution of 50 g of 2,2-bis[4-(4-aminophenoxy)phenyl]propane in a mixed solvent of 150 g of toluene and 10 g of N-methyl-2-pyrrolidone was added dropwise to the reaction system over a period of 1 hour while maintaining the inner temperature at 75° to 80° C., followed by stirring at that temperature for 1 hour to conduct addition reaction.

Subsequently, 2.3 g of p-toluenesulfonic acid was added to the reaction mixture, and the mixture was heated at a toluene refluxing temperature (112° C.) for 7 hours to conduct cyclization of the maleamic acid while azeotropically removing produced water and toluene out of the system.

After completion of the reaction, 150 g of pure water was added to the reaction mixture, followed by stirring at 80° to 85° C. The above washing was repeated three times.

The washed reaction mixture was heated in an oil bath kept at 160° C. to distill off toluene at 116° to 140° C. under atmospheric pressure. When the amount of distilled toluene became small, the pressure was diminished to 5 mmHg, and distillation of toluene was further continued while maintaining at 140° C. until no toluene was distilled off any more.

The molten bismaleimide was withdrawn into an aluminum tray and cooled to solidify at room temperature to obtain 67.5 g of a yellowish brown bismaleimide (yield: 97.1%).

The resulting bismaleimide had a melting point of 65° to 72° C., a residual monomaleamic acid content of 1.9%, and a residual solvent content of 0.5%. The X-ray diffraction pattern showed a broad peak, and the non-crystallization rate was 100%. When 15 g of the resulting bismaleimide was dissolved in 45 g of tetrahydrofuran at room temperature, there was obtained a uniform solution.

COMPARATIVE EXAMPLE 2

The same procedure as in Example 7 was repeated, except that the washed reaction mixture was directly cooled to 30° C. without conducting distillation of toluene. The precipitate thus formed was collected by filtration and dried at 70° C. for 48 hours. There was obtained 67.6 g (apparent yield: 97.2%) of a pale yellow maleimide powder.

The resulting maleimide contained 13.1% toluene and 1.8% monomaleamic acid, had a melting point of 140° to 145° C., and exhibited a non-crystallization rate of 0%.

COMPARATIVE EXAMPLE 3

In the same flask as used in Example 7 were charged 40 g of 2,2-bis[4-(4-aminophenoxy)phenyl]propane and 230 g of acetone, and the inner temperature was adjusted to 20° C. Then, 21.1 g of maleic anhydride was added thereto in small portions over a period of 30 minutes. After the addition, the mixture was stirred for 30 minutes to conduct addition reaction.

To the reaction mixture were added 26.1 g of acetic anhydride, 5 ml of triethylamine, and 0.4 g of nickel acetate, and the temperature was elevated up to 65° C., at which cyclization of the maleamic acid was conducted for 2 hours.

After completion of the reaction, the reaction mixture was cooled to room temperature and then added dropwise to 1000 ml of pure water to precipitate crystals. The crystals were collected by filtration, washed twice with 1000 ml portions of pure water, and dried to obtain 49.0 g (yield: 88.1%) of a yellow bismaleimide. The resulting bismaleimide had a residual solvent content of 0.3%, a residual monomaleamic acid content of 9.8%, and a melting point of 78° to 85° C.

In a four-necked flask were charged 49 g of the above prepared bismaleimide and 125 g of acetone, followed by stirring at 65° C. to form a uniform solution. The solution was cooled to room temperature to recrystallize. The crystals were collected by filtration and dried at 70° C. for 24 hours to obtain 28.3 g of a pale yellow bismaleimide.

The resulting bismaleimide had a residual monomaleamic acid content of 2.8%, a residual solvent content of 0.3%, a melting point of 143° to 145° C., and a non-crystallization rate of 0%. Fifteen grams of the resulting bismaleimide in 45 g of tetrahydrofuran did not gave a solution.

While the invention has been described in detail and with reference to specific examples thereof, it will be apparent to one skilled in ! the art that various changes and modifications can be made therein without departing from the spirit and scope thereof.

What is claimed is:

1. A non-crystalline ether-imide high purity bismaleimide represented by formula (I):

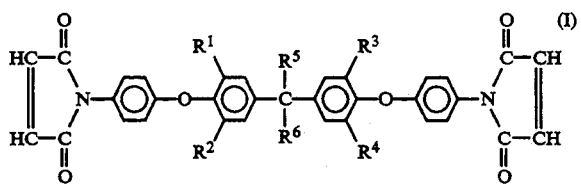

wherein $R^1$, $R^2$, $R^3$, and $R^4$ each represent a hydrogen atom, a halogen atom, or an alkyl group having from 1 to 4 carbon atoms; $R^5$ represents a hydrogen atom or a methyl group; and $R^6$ represents a hydrogen atom, a methyl group or a phenyl group; wherein said purity is not less than 95% by weight.

2. A bismaleimide composition as claimed in claim 1, wherein a non-crystalline bismaleimide represented by formula (I) is present in a proportion of not less than 50% by weight based on the total bismaleimide represented by formula (I).

3. A bismaleimide composition as claimed in claim 1, wherein said composition shows a peak of heat of fusion at 75°±5° C. and/or 85°±5° C. in differential thermal analysis with a differential scanning calorimeter, with the ratio of the peak area in temperatures of 120° C. or higher to the total peak area being not more than 50%.

4. A process for producing a non-crystalline ether-imide high purity bismaleimide represented by formula (I):

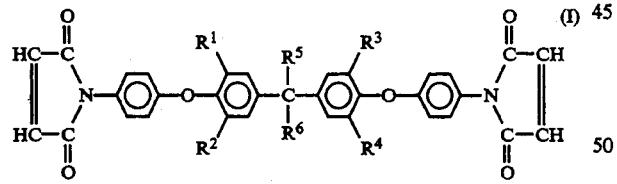

wherein $R^1$, $R^2$, $R^3$, and $R^4$ each represent a hydrogen atom, a halogen atom, or an alkyl group having from 1 to 4 carbon atoms; $R^5$ represents a hydrogen atom or a methyl group; and $R^6$ represents a hydrogen atom, a methyl group or a phenyl group, comprising completely melting a crystalline bismaleimide represented by formula (I) and rapidly cooling the molten bismaleimide at a rate of 5° C./minute or more to solidify, wherein said purity is not less than 95% by weight.

5. A process as claimed in claim 4, wherein said melting is carried out by melt-kneading at a temperature not lower than the melting point of the crystalline bismaleimide.

6. A process for producing a non-crystalline ether-imide high purity bismaleimide composition represented by formula (I):

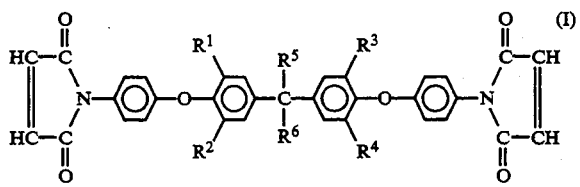

wherein $R^1$, $R^2$, $R^3$, and $R^4$ each represent a hydrogen atom, a halogen atom, or an alkyl group having from 1 to 4 carbon atoms; $R^5$ represents a hydrogen atom or a methyl group; and $R^6$ represents a hydrogen atom, a methyl group or a phenyl group, comprising addition reacting at a temperature of from 70° to 150° C. an aromatic ether diamine represented by formula (II):

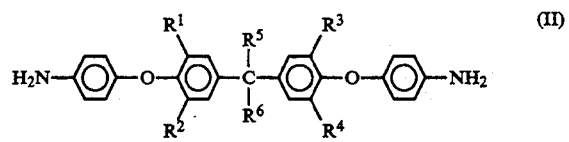

wherein $R^1$, $R^2$, $R^3$, $R^4$, $R^5$, and $R^6$ each has the same meaning as defined in formula (I), and maleic anhydride in a mixed solvent of an aromatic hydrocarbon having from 6 to 10 carbon atoms and an aprotic polar solvent selected from the group consisting of an amide compound, a sulfur-containing compound and phosphorus-containing compound in an amount of 0.1 to 30% by weight based on the total solvent to obtain a maleamic acid, heating the resulting maleamic acid at a temperature of from 80° to 150° C. to effect dehydrating cyclization in the presence of an inorganic or organic acid catalyst while azeotropically removing by-produced water with the aromatic hydrocarbon solvent, removing the remaining solvent by distillation maintaining a uniform solution, withdrawing the produced maleimide in a molten state, and rapidly cooling the maleimide at a rate of 5° C./minute or more to solidify, wherein said purity is not less than 95% by weight.

7. A process for producing a non-crystalline ether-imide high purity bismaleimide represented by the formula (I):

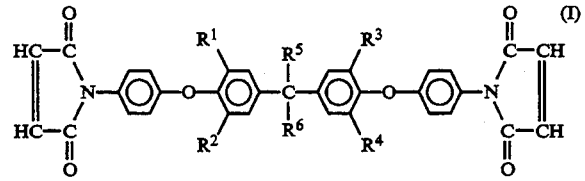

wherein $R^1$, $R^2$, $R^3$, and $R^4$ each represent a hydrogen atom, a halogen atom, or an alkyl group having from 1 to 4 carbon atoms; $R^5$ represents a hydrogen atom or a methyl group; and $R^6$ represents a hydrogen atom, a methyl group or a phenyl group, comprising uniformly dissolving a crystalline bismaleide represented by formula (I) in an organic solvent selected from the group consisting of aromatic hydrocarbons, esters, ethers, ketones and aprotic polar solvents, heating the uniform solution at 80° C. or higher to distill off the organic solvent, and cooling the molten residue to solidify at a rate of 5° C./minute or more, wherein said purity is not less than 95% by weight.

* * * * *